(12) United States Patent
Noel

(10) Patent No.: US 7,055,575 B2
(45) Date of Patent: *Jun. 6, 2006

(54) THERMALLY ACTIVE CONVECTION APPARATUS

(76) Inventor: Thomas P. Noel, 500 E. Greenwich Ave., Unit 129, West Warwick, RI (US) 02893

(*) Notice: Subject to any disclaimer, the term of this patent is extended or adjusted under 35 U.S.C. 154(b) by 0 days.

This patent is subject to a terminal disclaimer.

(21) Appl. No.: 10/463,055

(22) Filed: Jun. 17, 2003

(65) Prior Publication Data

Related U.S. Application Data

(63) Continuation-in-part of application No. 10/274,161, filed on Oct. 18, 2002, now Pat. No. 6,904,956.

(51) Int. Cl.
*F28D 19/00* (2006.01)
*F28F 7/00* (2006.01)

(52) U.S. Cl. .................................. 165/10; 165/104.17

(58) Field of Classification Search ................ 165/10, 165/104.15, 104.17, 104.19, 104.21, 141, 165/154, 901, 902, 903, 104.18
See application file for complete search history.

(56) References Cited

U.S. PATENT DOCUMENTS

| | | | |
|---|---|---|---|
| 2,595,328 A | | 5/1952 | Bowen |
| 3,683,152 A | * | 8/1972 | Laing et al. ............... 219/213 |
| 4,335,781 A | | 6/1982 | Duffy |
| 4,355,627 A | * | 10/1982 | Scarlata ................... 126/400 |
| 4,361,182 A | * | 11/1982 | Michalak .................. 165/10 |
| 4,561,493 A | | 12/1985 | Yanadori et al. |
| 4,753,241 A | * | 6/1988 | Brannigan et al. .......... 607/112 |
| 4,976,308 A | * | 12/1990 | Faghri ........................ 165/10 |
| 5,000,252 A | * | 3/1991 | Faghri ........................ 165/10 |
| 5,036,904 A | | 8/1991 | Kanda et al. |
| 5,069,208 A | | 12/1991 | Noppel et al. |
| 5,163,504 A | | 11/1992 | Resnick |
| 5,650,090 A | * | 7/1997 | Salyer ........................ 252/70 |
| 5,840,080 A | | 11/1998 | Der Ovanesian |
| 6,074,415 A | | 6/2000 | Der Ovanesian |
| 6,230,788 B1 | | 5/2001 | Choo et al. |
| 6,439,298 B1 | * | 8/2002 | Li ........................ 165/104.33 |
| 6,904,956 B1 | * | 6/2005 | Noel .................... 165/104.19 |

FOREIGN PATENT DOCUMENTS

| | | |
|---|---|---|
| JP | 0041358 | 9/1978 |
| JP | 0207793 | 6/1981 |
| JP | 0000490 | 1/1982 |
| JP | 0188990 | 11/1982 |
| JP | 0038593 | 2/1989 |
| JP | 2287096 | 11/1990 |

* cited by examiner

*Primary Examiner*—Tho Duong
(74) *Attorney, Agent, or Firm*—Tod R. Nissle, P.C.

(57) ABSTRACT

Apparatus for abstracting heat comprises a container charged with a first liquid and with small auxiliary containers free to circulate in the first liquid. Each of the small auxiliary containers is charged with a second liquid. The first and second liquids each have a selected temperature of transformation that facilitates use of the apparatus to heat or cool a substance contacted by the apparatus.

3 Claims, 6 Drawing Sheets

THERMALLY ACTIVE CONVECTION APPARATUS

This is a continuation-in-part of application Ser. No. 10/274,161, filed Oct. 18, 2002, now U.S. Pat. No. 6,904,956.

CROSS REFERENCE TO RELATED APPLICATIONS

N/A.

STATEMENT REGARDING FEDERALLY SPONSORED RESEARCH OR DEVELOPMENT

N/A.

INCORPORATION-BY-REFERENCE OF MATERIAL SUBMITTED ON A COMPACT DISC (See 37 CFR 1.52(e)(5) and MPEP 608.05

N/A.

BACKGROUND OF THE INVENTION (1) Field of the Invention.

This invention pertains to apparatus and methods for abstracting heat from a substance.

More particularly, the invention pertains to an improved apparatus and method which utilizes a matrix comprised of liquids and solids to abstract, over an extended period of time, heat from a substance.

In a further respect, the invention pertains to an improved apparatus of the type described which utilizes a plurality of heat transfer elements having three dimensional parity.

In another respect, the invention pertains to an improved heat abstracting apparatus of the type described which convects heat along paths intermediate spaced apart heat transfer elements.

In still a further respect, the invention pertains to an improved apparatus and method of the type described in which heat transfer elements are shaped to absorb heat along vertical and lateral paths.

In still another respect, the invention pertains to an improved simplified method of manufacturing a heat transfer device.

In yet a further respect, the invention pertains to an improved heat abstracting apparatus of the type described which provides efficient transfer using a single heat transfer element—liquid interface.

(2) Description of Related Art including information disclosed under 37 CFR 1.97 and 1.98.

So called "cold packs" are well known and typically, for example, comprise pliable, hollow, vinyl containers filled with a gelatin. In use, the cold pack is frozen and is placed against an individual's neck or other part of the individual's body to cool the individual. One such conventional cold pack is marketed under the trademark "THERAPAC" and comprises a twelve inch-by-twelve inch two ply vinyl container filled with a white odorless insoluble gelatin. Another conventional cold pack is marketed under the trademark "COLPAC" and comprises a twelve inch-by-twelve inch single ply polymer container filled with a gray odorless soluble gelatin. Such conventional cold packs are widely disseminated and effectively absorb heat. One principal disadvantage of such cold packs is that they have a relatively short-lived ability to stay cold. For example, when the THERAPAC and COLPAC cold packs noted above are removed from a freezer, the temperature on the outer surface of the cold pack can be five degrees F. After about an hour, the temperature can be about forty-five to fifty degrees F. After about two hours, the temperature on the outer surface of the cold packs can be about fifty-two to fifty-eight degrees F. After about three hours, the temperature can be about sixty-five to seventy degrees F. Consequently, after only an hour the temperature of the outer surface of each of the cold packs is well above freezing.

Accordingly, it would be highly desirable to provide an improved cold pack which would, after being exposed to ambient temperature, maintain a low temperature for an extended period of time.

Therefore, it is a principal object of the invention to provide an improved apparatus for abstracting heat from a solid, liquid, gas or other substance.

A further object of the instant invention is to provide an improved cold pack which will maintain a cold temperature for an extended period of time after being exposed to a temperature greater than that of the cold pack.

Another object of the invention is to provide an improved method for manufacturing a cold pack.

Still a further object of the invention is to provide a heat transfer device that facilitates conforming the device to the contour of the body.

Still another object of the invention is to provide an improved heat transfer device with a module matrix that facilitates folding the device and partitioning the device.

BRIEF DESCRIPTION OF THE SEVERAL VIEWS OF THE DRAWING(S)

These and other, further and more specific objects and advantages of the invention will be apparent to those skilled in the art from the following detailed description thereof, taken in conjunction with the drawings, in which.

BRIEF DESCRIPTION OF THE INVENTION

Figure 1:
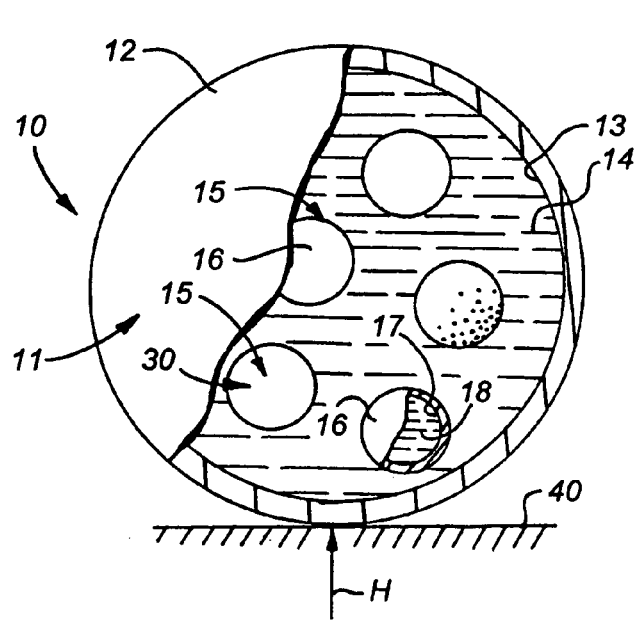
FIG. 1 is an elevation view illustrating a heat transfer device constructed in accordance with the principles of the invention.

Briefly, in accordance with the invention, I provide an improved heat transfer device for use in contacting and drawing heat away from a substance. The heat transfer device includes a hollow primary container including a wall, and a first liquid housed in the container; and, includes at least one hollow auxiliary container in the first liquid and including a wall, and a second liquid housed in the auxiliary container. The second liquid has a freezing point less than the freezing point of the first liquid.

In another embodiment of the invention, I provide an improved method for cooling a substance. The method includes the steps of providing a heat transfer device. The heat transfer device includes a hollow primary container including a wall, and a first liquid housed in the container. The primary container also includes at least one hollow auxiliary container in the first liquid. The auxiliary container includes a wall, and a second liquid housed in the auxiliary container. The second liquid has a freezing point less than the freezing point of the first liquid. The method also includes the steps of cooling the heat transfer device to freeze the second liquid; and, contacting the substance with the heat transfer device.

In a further embodiment of the invention, I provide an improved method for cooling a substance. The method includes the step of providing a heat transfer device. The heat transfer device includes a hollow primary container. The primary container includes a wall, and a first liquid housed in the container. The primary container also includes at least one hollow auxiliary container in the first liquid. The hollow auxiliary container includes a wall, and a second liquid housed in the wall of the auxiliary container. The second liquid has a freezing point less than the freezing point of the first liquid. The method also includes the steps of cooling the heat transfer device to freeze the second liquid; and, contacting the substance with the heat transfer device such that heat is abstracted from the substance into the first liquid by conduction through the wall of the primary container, such that heat abstracted into the first liquid by conduction through the wall of the primary container causes the liquid to have a nonuniform temperature and produces circulatory motion in the liquid due to variation in the density of the liquid and the action of gravity, and such that heat is abstracted from the first liquid by the conduction through the wall of the auxiliary container.

In still another embodiment of the invention, I provide an improved two phase single wall heat transfer device for use in contacting and drawing heat away from a substance. The heat transfer device includes an outer wall circumscribing and enclosing an inner space; a plurality of hollow fluid tight containers connected to a portion of said wall and extending from the wall into the inner space; a first heat-exchange composition in the inner space contacting each of the fluid tight containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation.

In still a further embodiment of the invention, I provide an improved two phase single wall bi-directional heat transfer device for use in contacting and drawing heat away from a substance. The heat transfer device includes an outer wall circumscribing and enclosing an inner space; a plurality of hollow fluid containers mounted on the outer wall in the inner space, each of the containers including a top and at least one side; a first heat-exchange composition in the inner space contacting each of the fluid containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation. The side of each of the hollow fluid tight containers is substantially normal to the top such that heat traveling through the hollow fluid container between the first and second heat-exchange compositions travels in a first direction through the top and in a second direction through the side. The first direction is substantially normal to the second direction.

In yet another embodiment of the invention, I provide an improved two phase single wall heat transfer device for use in contacting and drawing heat away from a substance. The heat transfer device includes an outer wall circumscribing and enclosing an inner space; a plurality of spaced apart hollow fluid containers mounted in said inner space above said outer wall, each of said containers including a top and at least one side; a floor interconnecting the hollow fluid tight containers; a first heat-exchange composition in the inner space contacting each of the fluid containers and comprising a liquid which undergoes a change of state from the liquid phase to the solid phase at a selected temperature of transformation; a second heat-exchange composition in each of said hollow containers comprising a liquid which undergoes a change of state from the liquid phase to the solid phase at a selected temperature of transformation; the wall, floor, and fluid containers being shaped and dimensioned such that heat absorbed through the wall by the first heat-exchange composition is carried by convection intermediate the hollow fluid containers and into contact with the sides of the containers and with the floor.

In yet a further embodiment of the invention, I provide an improved two phase single wall heat transfer device for use in contacting and drawing heat away from a substance. The heat transfer device includes an outer wall circumscribing and enclosing an inner space; a plurality of hollow fluid containers mounted in the inner space; a first heat-exchange composition in the inner space contacting each of the fluid containers and comprising a liquid which undergoes a change of state from the liquid phase to the solid phase at a selected temperature of transformation; a second heat-exchange composition in each of hollow containers comprising a liquid which undergoes a change of state from the liquid phase to the solid phase at a selected temperature of transformation; and, a pump for circulating the first heat-exchange composition into contact with the fluid containers.

In still yet another embodiment of the invention I provide an improved pliable two phase single wall heat transfer device for use in contacting and drawing heat away from a substance. The heat transfer device comprises an outer wall circumscribing and enclosing an inner space; a plurality of spaced apart hollow fluid tight containers connected to a portion of the wall, extending from the wall into the inner space, and including rounded bottoms to faciliate folding adjacent ones of the fluid containers against one another;a first heat-exchange composition in the inner space contacting each of the fluid tight containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation.

In yet still a further embodiment of the invention, I provide an improved method for manufacturing a two phase single wall bi-directional heat transfer device for use in contacting and drawing heat away from a substance. The improved method includes the steps of providing a first sheet of pliable material; forming a pan with the sheet of material, the pan including a peripheral lip extending around the pan; charging the pan with a first heat-exchange composition comprising a liquid which undergoes a change of state from the liquid phase to the solid phase at a selected temperature of transformation; providing a second sheet of pliable material; forming a module matrix with the second sheet of material, the module matrix including a peripheral edge and including a plurality of modules each with a bottom and an open top; placing the module matrix in the pan such that the bottom of each module extends into the first heat-exchange composition; administering a second heat-exchange composition to each of the modules comprising a liquid which undergoes a change of state from the liquid phase to the solid phase at a selected temperature of transformation liquid; and, sealing the first composition in the pan and the second composition in the module matrix.

In another embodiment of the invention I provide an improved pliable two phase single wall heat transfer device for use in contacting and drawing heat away from a substance. The heat transfer device comprises an outer wall circumscribing and enclosing an inner space; a plurality of spaced apart hollow fluid tight containers connected to a portion of the wall, extending from the wall into the inner space, and including rounded bottoms to faciliate folding adjacent ones of the fluid containers against one another; a first heat-exchange composition in the inner space contacting each of the fluid tight containers and comprising a liquid which undergoes a change of state from the liquid phase to the solid phase at a selected temperature of transformation; and, a second heat-exchange composition in each of the hollow containers comprising a liquid which undergoes a change of state from the liquid phase to the solid phase at a selected temperature of transformation. A plurality of channels interconnects pairs of the hollow containers to promote the flow of liquid therebetween.

DETAILED DESCRIPTION OF THE INVENTION

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates a heat transfer device generally identified by reference character 10. Device 10 includes a spherical hollow primary container having a wall 11 including spherical outer surface 12 and spherical inner surface 13. A liquid 14 is housed inside the primary container. At least one auxiliary spherical hollow container 15 is in and free to move and circulate about the reservoir formed by liquid 14. Each hollow container 15 includes a spherical wall 30 having a spherical outer surface 16 and a spherical inner surface 17. A liquid 18 is housed inside each auxiliary container 15. Liquid 14 has a lower (cooler) freezing point than liquid 18, and preferably, but not necessarily, has a freezing point lower than the coldest temperatures found in conventional household or commercial freezers. By way of example, and not limitation, liquid 14 presently comprises propylene glycol and liquid 18 comprises water. Liquid 18 preferably has a freezing point greater or equal to the coldest temperature found in conventional household or commercial freezers.

Other examples of compositions that can be utilized as liquid 14 or liquid 18 include aqueous solutions of ethyl alcohol, methyl alcohol, PRESTONE, iso-propyl alcohol, and glycerol. Magnesium chloride, sodium chloride, and calcium chloride brines can be utilized. Refrigerants which can be utilized as liquid 14 include ammonia, ethyl chloride, and methyl chloride.

The wall 11 is preferably, although not necessarily, fabricated from a pliable vinyl or other pliable material so that wall 11 will conform to a part of an individual's body or will conform to some other object that is contacted by heat transfer device 10. Similarly, the wall 30 is preferably, although not necessarily, fabricated from a pliable vinyl or other pliable material so that wall 30 will conform to a part of an individual's body or will conform to some other object. As would be appreciated by those of skill in the art, device 10 and walls 11 and 15 need not be spherical and can be made to have any desired shape, contour, and dimension. Walls 11 and 15 need not be pliable and can be substantially rigid.

In use of the heat transfer device 10, device 10 is placed in a freezer. Liquid 18, being water, freezes. Liquid 14, being propylene glycol, does not freeze. After liquid 18 freezes, device 10 is removed from the freezer and placed against a portion 40 of an individual's body or against some other object or substance so that device 10 absorbs heat H. Heat is absorbed through wall 11 and into liquid 14 by the transfer of kinetic energy from particle to particle. When heat is absorbed by liquid 14, liquid 14 has a non-uniform temperature, i.e., liquid near wall 11 is warmer and has a greater enthalpy than liquid farther away from wall 11. If liquid near wall 11 has a different temperature, the density of the liquid near wall 11 is different than the density of cooler liquid farther away from wall 11. This density differential, along with the force of gravity, causes circulation and movement of liquid 14. When, during this circulation and movement, warmed liquid 14 passes by and contacts an auxiliary spherical hollow container 15, heat is absorbed through wall 30 and into frozen liquid 18 by the transfer of kinetic energy from particle to particle.

Figure 2:
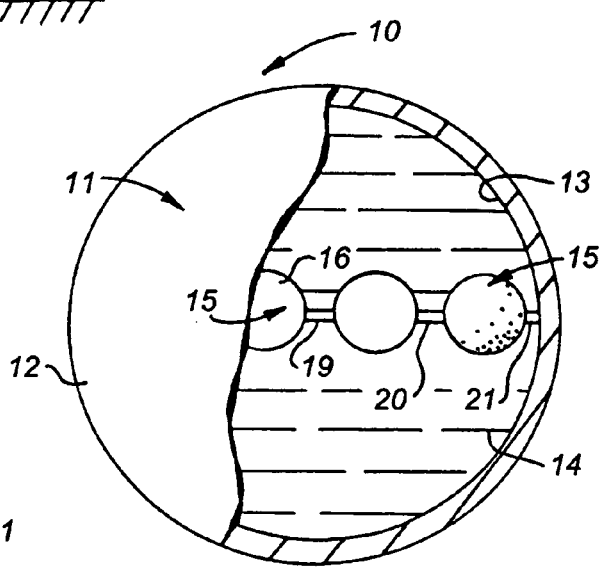
FIG. 2 is an elevation view illustrating an alternate embodiment of the invention.

The heat transfer device of FIG. 2 is identical to that of FIG. 1 except that auxiliary containers 15 are connected in a chain to each other and to the inner surface of wall 13 by links 19, 20, and 21, respectively. This chain can be slack so that containers 15 can, to a degree, move about in liquid 14, or, the chain can be substantially rigid so it maintains its shape and dimension even if pliable wall 11 is displaced.

Figure 3:
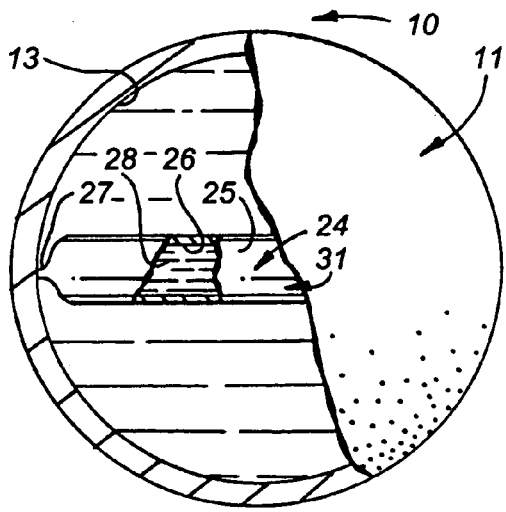
FIG. 3 is an elevation view illustrating yet another embodiment of the invention.

The heat transfer device of FIG. 3 is identical to that of FIG. 1 except that auxiliary containers 15 are removed and replaced by an elongate hollow auxiliary container 31 having a cylindrical wall 24 with a cylindrical outer surface 25 and a cylindrical inner surface 26. Container 31 is filled with a liquid 28 which, like liquid 18, has a freezing point which is greater (warmer) than that of liquid 14.

In another embodiment of the invention, liquids 18 and/or 28 have a freezing point which is less than that of liquid 14. This embodiment of the invention is particularly desirable if liquid 14, when frozen, is malleable or is readily broken into pieces which permit a pliable wall 13 to be displaced and manipulated like the pliable rubber wall of a hot water bottle can be manipulated when the water bottle is filled with water In a further embodiment of the invention, liquids 18 and/or 28 have a freezing point equivalent to that of liquid 14.

The use of the devices of FIGS. 2 and 3 is comparable to that of the heat transfer device of FIG. 1. In FIG. 2, auxiliary containers 15 absorb heat from liquid 14. In FIG. 3, auxiliary container 31 absorbs heat from liquid 14.

The ratio of the mass of liquid 14 with respect to the mass of liquid 18 (or 28) in a device 10 can vary as desired, but is presently preferably about 1:1. As the mass of liquid 18 with respect to the mass of liquid 14 increases, the heat absorbing capacity of liquid 18 increases, but there is less of liquid 14 to circulate to containers 15 heat which is absorbed from wall 11. It is believed that if the mass of liquid 18 greatly exceeds that of liquid 14 (e.g., the ratio of liquid 18 to liquid 14 is, for example, 8:1), then heat will tend to be absorbed directly by containers 15 instead of first being absorbed by liquid 14 and transferred to containers 15. This would defeat a primary feature of the invention. The use of liquid 14 to circulate heat to containers 15 is believed central to the invention and is believed, at least in part, responsible for why the heat transfer apparatus of the invention stays cool for unusually long periods of time. The ratio of liquid 18 to liquid 14 is preferably, but not necessarily, in the range of 3:1 to 1:3, most preferably in the range of 2:1 to 1:2.

The materials utilized to construct walls 11 and 30 and 24 affect the rate of heat transfer. Thicker walls normally transfer heat at a slower rate; thinner walls at a faster rate. While polymer material is desirable in walls 11, 24, 30 because pliable polymer materials are readily available, incorporating metal or other materials which facilitate the transfer of heat is also desirable.

When a device 10 is placed in a freezer to solidify liquid 18, liquid 14 can have a composition which permits it to turn to a gel, but preferably does not solidify. It is preferred that liquid 14 remain a liquid or become a gel so that device 10 remains pliable after being frozen. Similarly, when liquid 18 is frozen, it may turn to a gel and may not completely solidify.

The following example is given by way of demonstration and not limitation of the scope of the invention.

EXAMPLE

The following were obtained:
1. A twelve inch long by twelve inch wide "THERAPAC" (™) two ply vinyl "cold pack" containing a white odorless insoluble gelatin. This cold pack was identified as "A".
2. A twelve inch long by twelve inch wide "COLPAC" (™) single ply plastic "cold pack" filled with a gray odorless soluble gelatin. This cold pack was identified as "B".
3. A cold pack was constructed in accordance with the invention and comprised a ten inch long by ten inch wide two ply plastic container filled with one and three-fourths pounds of propylene glycol and a plurality of small elastic liquid-filled rubber containers each having a diameter in the range of one inch to one and one-quarter inches. The liquid in each of the small rubber containers was water.

One and three-fourths pounds of water was used to fill the small rubber containers, i.e., each small rubber container contained significantly less than one and three-fourths pounds of water, and, if all the water in all of the small rubber containers were poured in a container, the water would have weighed one and three-fourth pounds. The rubber containers could move about freely in the propylene glycol. Each ply in the plastic bag had a thickness of about two to three mils. The wall thickness of each rubber container was about two to three mils. This cold pack was identified as "C".

Cold packs A, B, C were all placed at the same time in a freezer. After several hours, cold packs A, B, C were removed at the same time from the freezer and placed on a flat table top in a room. The room temperature was eighty degrees and was maintained at eighty degrees while the following measurements were made. Measurements were made when the cold packs were removed from the freezer and at hourly intervals thereafter up to four hours. Each time measurements were taken, a measurement was taken on the outer surface of each cold pack and on the interior of each cold pack. The results are summarized below in Tables I and II.

TABLE I

Surface Temperature Measurements of Cold Packs A, B, C

| | Temperature Measurements (Degrees F.) | | | | |
|---|---|---|---|---|---|
| Cold Pack | At removal | 1 hour | 2 hours | 3 hours | 4 hours |
| A | 5 | 48 | 56 | 72 | 77 |
| B | 5 | 47 | 55 | 73 | 80 |
| C | 10 | 39 | 39 | 40 | 42 |

TABLE II

Interior Temperature Measurements of Cold Packs A, B, C

| | Temperature Measurements (Degrees F.) | | | | |
|---|---|---|---|---|---|
| Cold Pack | At removal | 1 hour | 2 hours | 3 hours | 4 hours |
| A | 0 | 47 | 55 | 65 | 75 |
| B | 0 | 49 | 57 | 65 | 75 |
| C | 15 | 15 | 32 | 34 | 36 |

The above results demonstrate that the cold pack of the invention (identified as "C") remained much colder for much longer than the conventional cold packs identified as "A" and "B". These results were surprising and unexpected and are believed to demonstrate the utility and novelty of the heat transfer device of the invention.

Figure 4:
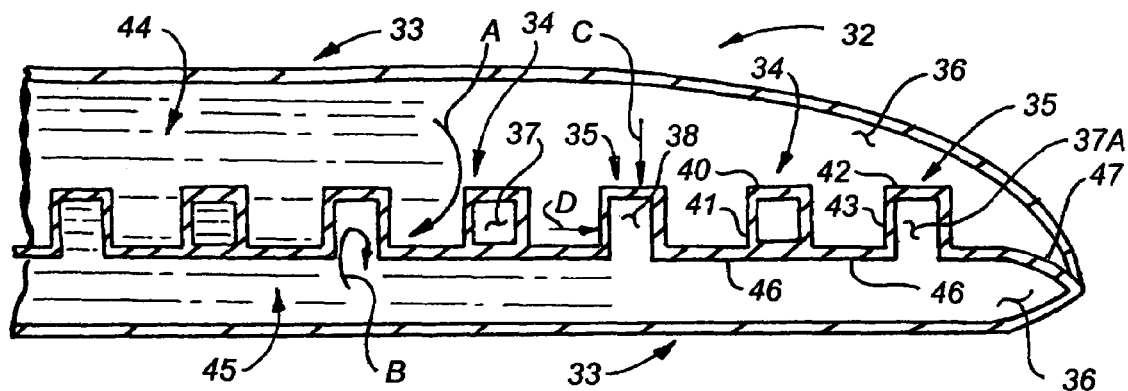
FIG. 4 is a side section elevation view illustrating still a further embodiment of the invention.

Another heat transfer device of the invention is illustrated in FIG. 4 and is generally indicated by reference character 32. Device 32 includes outer wall 33. The material(s) used to fabricate wall 33 can vary as desired. Wall 33 presently preferably comprises a pliable water impermeable material like rubber or plastic. Wall 33 circumscribes and encloses inner space 36. Cylindrical hollow fluid containers 34 and 35 are mounted in inner space 36. The shape and dimension of each container 34, 35 can vary as desired. Each container 34 is fluid tight and completely encloses a space 37. Each container 35 partially encloses a space 38 and opens into the lower portion of inner space 36 in FIG. 4. Each container 35 can be mounted on floor 46 in an inverted configuration in which space 38 opens into the upper portion—instead of the lower portion—of space 36. Each container 34 includes a top 40 and side 41. The thickness of top 40 and side 41 can vary as desired to vary the ability of heat to traverse and pass through top 40 and side 41.

Containers 34, 35 are mounted on a floor 46 that extends across and bifurcates inner space 36 into two separate chambers or spaces. The outer peripheral edge of floor 46 is attached to wall 33. A first heat-exchange composition 44 is in the upper chamber created in space 36 by floor 46. A second heat-exchange composition 45 is in the lower chamber created in space 36 by floor 46. Floor 46 and containers 34 and 35 prevent composition 44 from intermixing with composition 45, and vice-versa. If desired, floor 46 can be perforated to allow the flow of fluid 44 into fluid 45, and vice-versa.

The freezing point of composition 44 can vary as desired and can be equal to that of composition 45, greater than that of composition 45, or less than that of composition 45. In one presently preferred embodiment, the freezing point of composition 44 is lower than that of composition 45. Composition 44 can be the same as composition 45. It is presently preferred, although not necessary, that compositions 44 and 45 be in a liquid phase when heated to normal room temperature of 76 degrees F.; that composition 45 freeze at temperatures in the range of fifteen degrees Fahrenheit to thirty-two degrees Fahrenheit; and, that composition 44 freeze at temperatures less than fifteen degrees Fahrenheit. In this configuration, composition 45 normally freezes when placed in a conventional residential freezer while composition 44 does not. Since composition 44 then remains in a liquid state and since wall 33 normally is pliable, wall 33 and composition 44 can readily conform to a surface (i.e., the body of a human being or other animal) even if composition 45 is, when frozen, rigid.

A third heat-exchange chemical composition can be in space 37 in each fluid tight container 34. The third composition can be a gas, liquid, or solid and can have any desired phase transformation temperatures. Practically speaking, however, the third composition is, as are the first and second heat-exchange compositions, preferably a fluid at room temperature because the heat-exchange compositions preferred in the practice of the invention either remain in a fluid form or transform between only two phases, the liquid phase and the solid phase of the heat-exchange composition. Gases have minimal thermal capacity and ordinarily are difficult to transform into liquids or solids at normal ambient, freezing or heating temperatures.

When the upper portion of wall 33 in FIG. 4 is placed against a substance having a temperature cooler than that of an aqueous liquid composition 44, heat from composition 44 travels outwardly through wall 33 causing the temperature of the portion of composition 44 adjacent wall 33 to cool. When the composition 44 cools, the density of the cooled liquid increases, causing the liquid to move downwardly under gravity in a convection current in the direction of arrow A.

When the lower portion of wall 33 in FIG. 4 is placed against a substance having a temperature warmer than that of a liquid composition 45, heat from the substance is absorbed by composition 45 through the lower portion of wall 33. The warmed portion of composition 45 typically carries the heat by convection upwardly in the direction indicated by arrow B. Fluid circulating in the manner indicated by arrows A and B travels adjacent the sides 41, 43 and tops 40, 42 of containers 34 and 35, permitting heat to travel through the containers between compositions 44 and 45. The shape and configuration of containers 34 and 35 is important in this respect. A plurality of spaced apart containers 34 and 35 is preferred because the upstanding sides 41, 43 significantly increase the surface area available to compositions 44 and 45. Further, when sides 41 and 43 are substantially normal to floor 46 and top 40 or 42, heat can be absorbed substantially vertically through a top 40, 42 or floor 46 in the direction indicated by arrow C and can be absorbed substantially laterally through a side 41 and 43. A side 41, 43 is substantially normal to floor 46 or top, 40, 42 if the side is at an angle in the range of sixty to one-hundred and twenty degrees, preferably in the range of seventy-five to one-hundred and five degrees, to floor 46 or top 40, 42. In FIG. 4, sides 41 and 43 are normal to tops 40, 42 and floor 46. Another reason containers 34 and 35 are preferred is that when fluid flows between containers 34 and 35 or into a container 35, turbulent flow and eddy currents are believed more likely to occur, particularly if the distance between adjacent containers is one inch or less. Turbulent flow and eddy currents facilitate the intermixing of warmed fluid 44 (or 45) with cooler fluid 44 (or 45). This intermixing of fluid 44 having different temperatures facilitates the efficient transfer of heat from a substance to fluid 44 and from fluid 44 either through containers 34, 35 to composition 45 or to a third composition in spaces 37 in containers 34. Heat can also, if desired, transfer from composition 45 to fluid 44 in the event that composition 45 is used to absorb heat.

Another preferred feature of containers 34 and 35 is that each container have substantial dimensional parity. Dimension parity is important because it slows the absorption of heat by the container 34 and 35. Slowing the absorption of heat tends to extend the useful life of device 32 as a cooling device. If containers 34 and 35 do not have dimensional parity and instead take on the configuration of a sheet or panel, the composition in each container 34, 35 tends to more rapidly absorb heat. A container 34, 35 has dimensional parity when the height and width of a cross-section taken through the center (or estimated center) of the container and normal to the length (i.e., normal to the greatest dimension of the container) are substantially equal. The height and width of such a cross-section of the container are substantially equal when the ratio of the height to the width is in the range of 5:1 to 1:5, preferably 3:1 to 1:3. A sphere has substantial dimensional parity because the height and width of a cross-section through the center of the sphere are equal, i.e., are each equal the diameter of the sphere. Therefore, for a sphere, the ratio of the height of the cross-section to the width of the cross-section is 1:1. A cube has substantial dimensional parity because the ratio of the height to the width of a cross-section that passes through the center of the cube, passes through four of the corners of the cube, and is normal to a centerline passing through two corners of the cube is 1:1.

A parallelepiped that is 4 cm high, 6 cm wide, and 8 cm long has substantial dimensional parity because the ratio of height to the width of a cross-section taken through the center and normal to the longitudinal centerline of the parallelepiped 1:1.5.

A parallelepiped which is in the shape of a panel and has a length of 8 cm, height of 4 cm, and a width of 0.5 cm does not have substantial dimensional parity because the ratio of the height to the width of a cross-section taken through the center and normal to the longitudinal centerline of the parallelepiped is 8:1 (i.e., is 4 to 0.5). This parallelepiped would, because of its narrow width, more rapidly absorb heat and dissipate the thermal absorption capacity of the composition in or comprising the parallelepiped.

Figure 5:
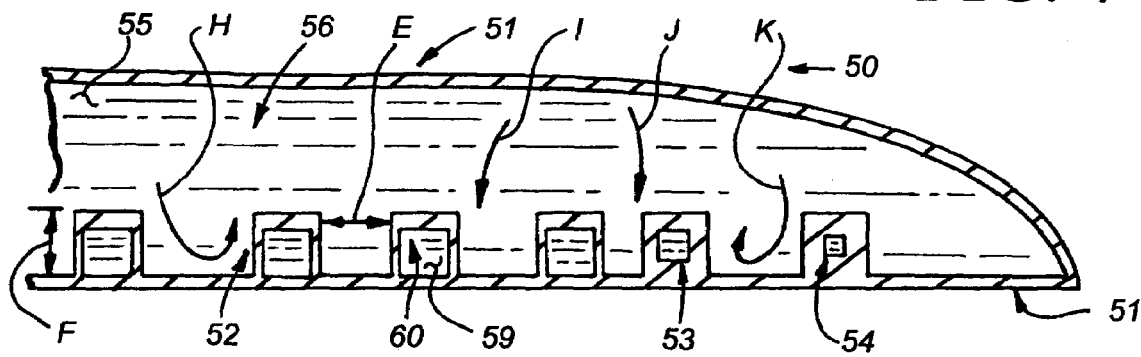
FIG. 5 is a side section elevation view illustrating still another embodiment of the invention.

When the side 41, 43 and top 40, 42 of a container 34, 35 are thin-walled, i.e., are less than about two millimeters (mm) thick (i.e., having a thickness of two mm plus or minus 10%), and have a substantially uniform thickness (i.e., the thickness of the side(s), top, and, if appropriate, bottom, walls at all points varies by no more than about two millimeters), then the outer dimensions of the container provide a good indication of whether the container has substantial dimensional parity. If, however, the thickness of a wall(s) of the container is greater than about two mm and/or the thickness of the walls is not substantially uniform, then the outer dimensions of the container may not provide a good indication of whether the container has substantial dimensional parity, and the configuration of the space 37, 37A inside the container 34, 35 needs to be taken into account to determine if there is substantial dimensional parity. The same criteria used to evaluate the dimensional parity of the outside shape and dimension of a container 34, 35 can be utilized to evaluate the dimensional parity of the space 37, 37A inside a container 34, 35. If the space 37, 37A is the shape of a cube, then the space has dimensional parity. If the space 37, 37A is the shape of a sphere, then the space has dimensional parity. If the space 37, 37A is the shape of a parallelepiped having a length of 8 cm, a height of 4 cm, and a width of 0.5, then the space does not have substantial dimensional parity. In FIG. 5, containers 53 and 54 are not thin-walled. Since, however, the cross-sections of the spaces inside containers 53 and 54 have the shape of a cube, containers 53 and 54 have substantial dimensional parity. The heat transfer container illustrated in U.S. Pat. No. 2,595,328 to Bowen does not appear to have substantial dimensional parity.

Figure 6:
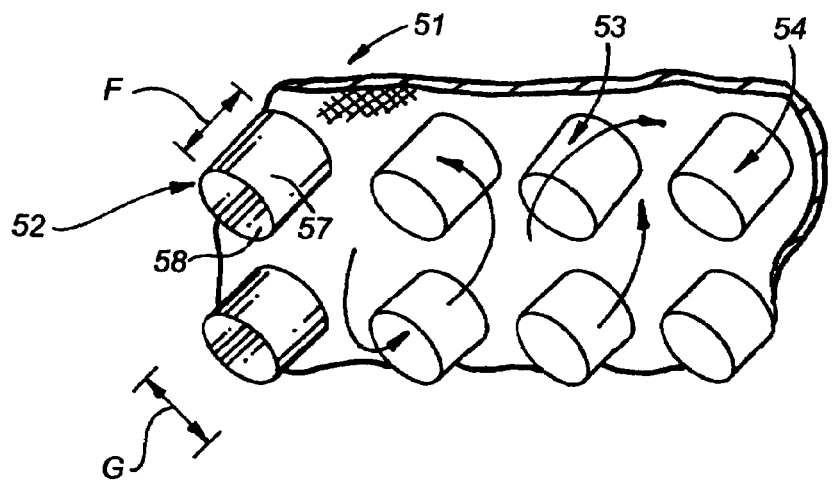
FIG. 6 is a perspective view illustrating a portion of the invention of FIG. 5.

Another heat transfer device 50 is illustrated in FIGS. 5 and 6 and is similar to heat transfer device 32. A particular advantage of device 50 is that it only requires outer liquid impermeable wall 51 and does not require a floor 46 because containers 52, 53, 54 are connected to a portion of wall 51 and extend into space. This makes device 50 inexpensive to manufacture. Each container 52, 53, 54 includes a fluid tight wall 57, a top 58, and a bottom that comprises a portion of wall 51. The inner space 60 of each container includes a heat-exchange composition 60. Inner space 55 is circumscribed and enclosed by wall 51 and includes heat-exchange composition 56. The freezing point of composition 56 can be greater than, less than, or equal to the freezing point of composition 60. In one presently preferred embodiment, the freezing point of composition 60 is a higher temperature than the freezing point of composition 56.

The distance, indicated by arrows E, between an adjacent pair of containers 52 can vary as desired, as can the height, indicated by arrows F, and the width, indicated by arrows G, of a container 52. To facilitate the transfer of heat between compositions 56 and 60, it is preferred that a plurality of containers 52 be provided. As the number of containers 52 increases, the available surface area increases. By way of example, and not limitation, containers 52 presently preferably have a width G in the range of one-quarter to one inch, and a height G in the range of one-quarter to one inch. This distance E between adjacent containers is in the range of one-quarter to three-quarters of an inch. Arrows H to K in FIG. 5 illustrate possible liquid flow paths. Liquid traveling along these flow paths transports heat by convection away from wall 51 toward containers 52, 53, 54.

Figure 7:
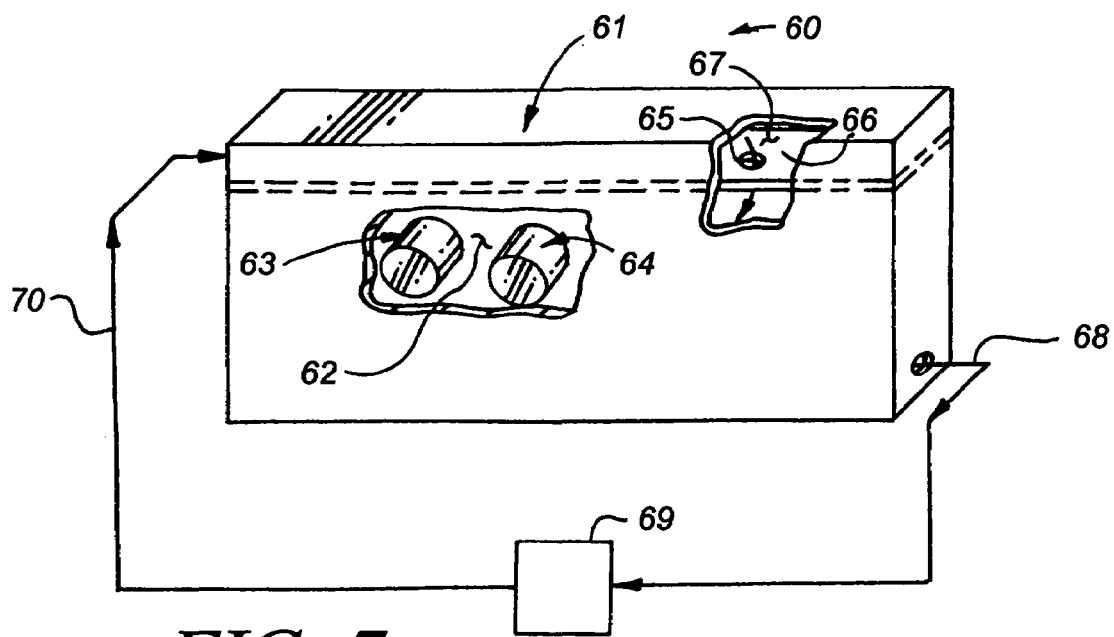
FIG. 7 is a perspective view illustrating yet a further embodiment of the invention.

Heat transfer device 60 in FIG. 7 includes parallelepiped wall 61 circumscribing and enclosing inner spaces 62 and 67 and hollow fluid tight containers 63, 64 mounted on wall 62. A heat-exchange fluid or solid is in each container 63, 64. Rectangular plate 66 separates spaces 62 and 67. Pump 69 circulates a heat-exchange liquid. The liquid flows out of space 62 in the direction of arrows 68, through pump 69, and back into space 67 in the direction of travel indicated by arrows 70. Liquid flowing into space 67 flows through perforations 65 back into space 62.

Figure 8:
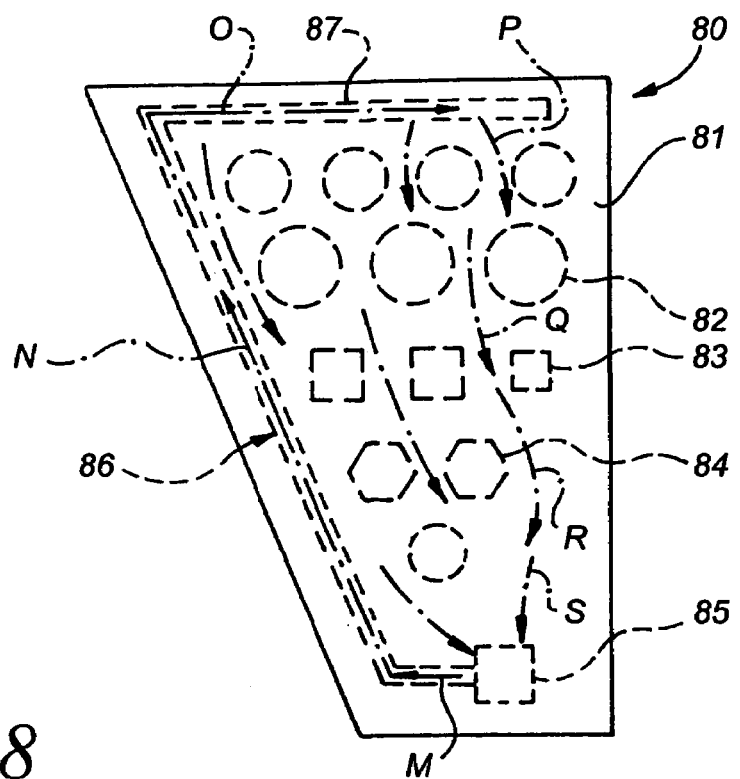
FIG. 8 is a top view illustrating yet another embodiment of the invention.

Heat transfer device 80 in FIG. 8 includes outer wall 81. Walls 61, 81 normally, but not necessarily, are liquid impermeable. Hollow fluid tight containers 82, 83, 84 are housed within wall 81, are mounted on wall 81, and extend into the inner space circumscribed by wall 81 in the same manner that containers 52, 53, 54 are attached to wall 51 and extend into space 55 in FIGS. 5 and 6. The inner space circumscribed by wall 81 is filled with a first heat-exchange composition. Each container 82 to 84 is filled with a second heat-exchange composition. When the first heat-exchange composition is in a fluid phase, pump 85 circulates the first heat-exchange composition. The first heat-exchange composition exits pump 85 and travels through conduit 86 in the manner indicated by arrows M, N, O. The upper arm 87 of conduit 86 is perforated such that fluid exits arm 87 under pressure in the direction indicated by arrow P. The perforations are shaped and spaced to facilitate a uniform rate of dispersal of fluid out of arm 87 along the length of arm 87, or along a selected portion of the length of arm 87. The first heat-exchange composition flows around and between containers 82, 38, 84 in the manner indicated by arrows Q, R, S and re-enters pump 85, which again directs the composition into conduit 86 under pressure.

Walls 33 and 51 and 61 and 81, floor 46, and containers 34, 35, 52, 53, 54, 63, 64, 82, 83, 84 can be rigid or flexible or pliable, elastic or non-elastic, porous or non-porous, fluid tight or not fluid tight, have one or more layers, and can be constructed from any desired material including, without limitation, resin, metal, glass, concrete, plaster, porcelain, and paper.

As earlier noted, fluid can be circulated in the heat transfer device of the invention by convection and by the use of a pump. Fluid can also be circulated by shaking the heat transfer device and by, when the outer wall 33, 51, 61, 81 is pliable, manually kneading or displacing the wall to move the heat-exchange composition 44, 56 in the device.

As will be appreciated by those of skill in the art, in FIG. 4 either the top or bottom of wall 33 can be placed against a surface to be heated or cooled. In FIG. 4, only containers 34 or only containers 35 can, if desired, be utilized and mounted on floor 46.

In one embodiment of the invention, the containers 52 in FIG. 5 each are cylindrically shaped, are of equivalent shape and dimension, have a diameter and height of about one-half inch, are equidistant from other adjacent containers, and are spaced apart about one-half inch in a checker board array similar to that shown in FIG. 6.

In FIG. 4, containers 34, 35 approximately double the surface area exposed to composition 44. If containers 34, 35 are not utilized and floor 46 is a flat, continuous member extending completely across device 32, then the surface area exposed to composition 44 is about equal to the sum of the area of the tops 40, 42 of the containers 34, 35 and the area of the portions of floor 46 extending intermediate containers 34, 35 in the manner shown in FIG. 4. When containers 34, 35 are utilized, the surface area exposed to composition 44 equals the sum of the area of tops 40, 42 plus the area of the portions of floor 46 extending intermediate containers 34, 35 plus the sum of the cylindrical surface areas of each side 41, 43. 100% of the surface area of each container 35 is in contact with composition 44. All of the surface area of each container 34 is in contact with composition 44 excepting the circular base, which is in contact with composition 45. The proportion of the surface area of each container 34, 35 in contact with composition 44 or 45 is in the range of 20% to 100%, preferably in the range of 55% to 100%, most preferably in the range of 70% to 100%. In U.S. Pat. No. 2,595,328 to Bowen, only 50% of each receptacle 8 is in contact with material 7 positioned above receptacle 8. The more desirable embodiments of the invention illustrated in FIGS. 4 and 5 herein utilize containers 34, 35 having well over 50% of the containers in contact with composition 44 and/or 45.

The use of containers 34, 35, 52, etc. that remain in fixed position comprises one preferred embodiment of the invention because the containers 34, 35, 52 are prevented from bunching together. This insures that the heat transfer characteristics of the heat transfer device remain fixed and more evenly distributed throughout the device.

Another important feature of the invention is the proportion of the surface area of floor 46 (or of the bottom area of a wall 51 on which containers 52, 53, 54 are mounted in FIG. 5) intermediate containers 34, 35 with respect to the surface area of floor 46 occupied by the base of each container 52, 53. This is important because there must be sufficient space intermediate containers 52, 53 to permit fluid to circulate in the manner indicated by arrows A and B (and arrows H to K in FIG. 5) so heat can be transferred through floor 46 to fluid 45 and/or through walls 41 and 43 to fluid 45 or to fluid in spaces 37. U.S. Pat. No. 2,595,328 discloses a heat transfer device which has little floor space (zones 9 in Bowen) and, consequently, which permits little lateral heat transfer and little heat transfer through zones 9. The ratio of the surface area of floor 46 intermediate containers 34, 35 to the surface area of the bases of containers 35, 35 (where in FIG. 4 the surface area of each base of a cylindrical containers 34, 35 is equal to the surface area of the top 40, 42 of the container) is in the range of 1:3.5 to 10:1, preferably 1:2 to 10:1.

Similarly the proportion of the surface area of containers 34, 35 that permits lateral heat transfer D is important in the practice of the invention. The proportion of the surface area of the side(s) of a container 34, 35 to the total surface area of the container is in the range of 1:4 to 10:1. The receptacles 8 in U.S. Pat. No. 2,595,328 to Bowen are not constructed to significantly utilize lateral heat transfer. The total surface area of container 35 herein includes the area of top 42 plus the area of side 43. The total surface area of container 34 includes the surface area of circular top 40, the surface area of cylindrical side 41, and the area of the circular base of container 34. If the proportion of the surface area of the side(s) of a container 34, 35 with respect to the total surface area of the container is too great (i.e., is, for example, 12:1), then it is likely the container is either losing dimensional parity or is so tall that it interferes with proper fluid circulation. Similarly if the proportion of the surface area of the side(s) of a container 34, 35 with respect to the total surface area of the container is too small (i.e., is for example 1:6), then it is also likely the container is losing dimensional parity and/or is so short that the lateral heat absorption D is adversely affected.

In one preferred embodiment of the invention, fluid 56 has a lower freezing point than the fluid in containers 52. For example, fluid 56 is glycol and the fluid 60 in containers 52 is water. Device 50 is placed in a conventional residential freezer in a refrigerator. Fluid 60 freezes. Fluid 56 does not. The upper portion of wall 51 in FIG. 5 is placed against the back of the neck of an individual. Since fluid 56 is in a liquid state, fluid 56 and the upper portion of pliable wall 51 readily conform to the shape of individual's neck (or shoulder, or arm, etc.). Fluid 56 absorbs heat. Convection currents H to K carry heat toward containers 52. The shape and dimension and spacing of containers 52 cause turbulent flow and eddy current when the convection currents flow into, past, and between containers 52. Frozen fluid 60 absorbs heat. Eventually a large enough quantity of heat is absorbed to cause frozen fluid 60 to undergo a phase transformation from a solid to a liquid.

Figure 9:
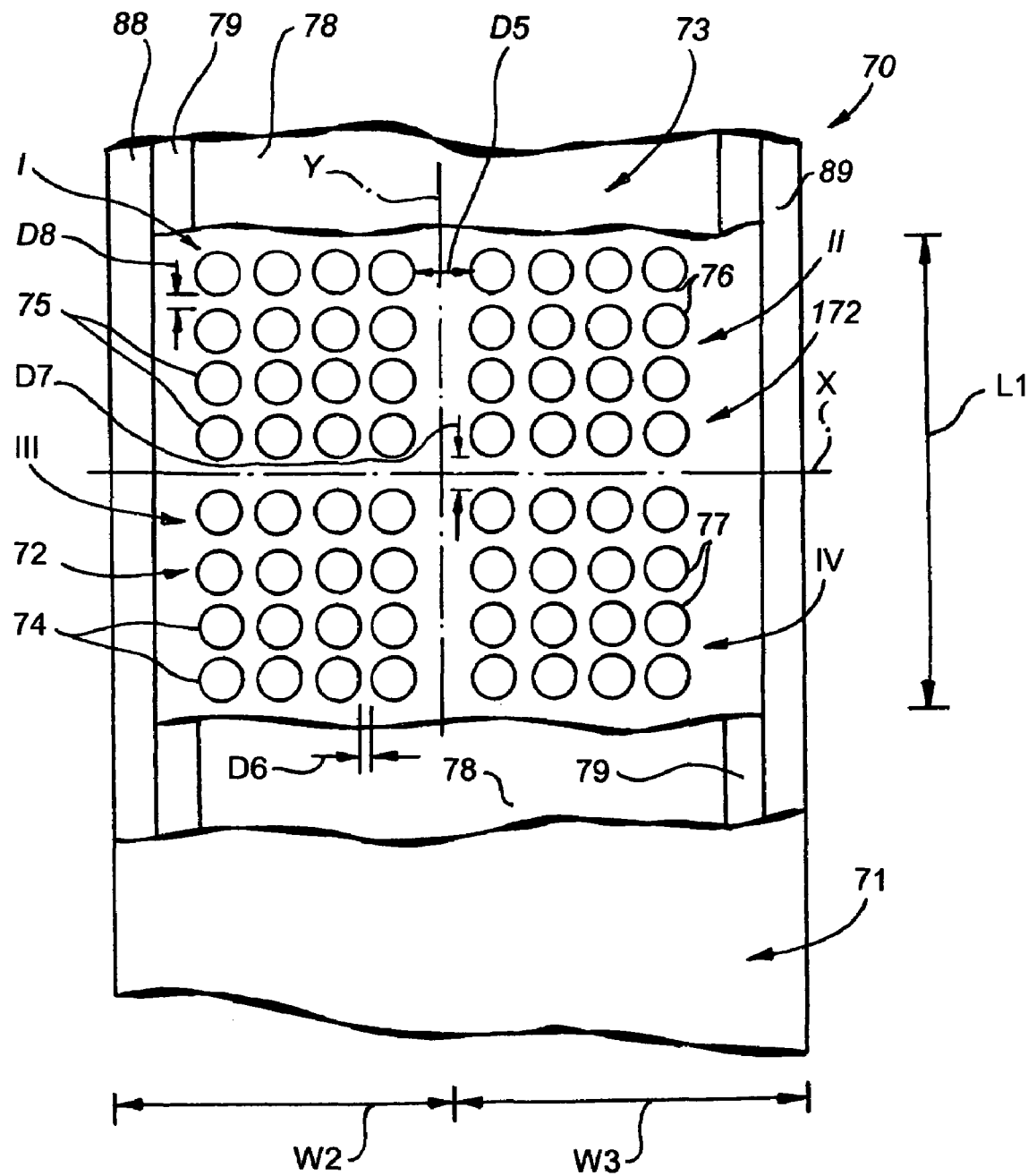
FIG. 9 is a top view illustrating still a further embodiment of the invention.

FIG. 9 illustrates another heat transfer device 70 constructed in accordance with the principles of the invention. Device 70 includes a pan 73, a module matrix 72, and a seal layer 71.

Pan 73 includes bottom 78 and includes outer parallel elongate planar lips or edges 88 and 89 and includes inner parallel inset elongate planar lips or edges 79. The construction of lips or edges 88, 89, 79 is similar to the construction of lips or edges 88A, 89A, 79A and 79B in pan 173A in FIG. 10C. The construction of pan 73 is similar to that of pan 173A.

Module matrix 172 includes a plurality of modules 74, 75, 76, 77. In FIG. 9 there are sixteen equal sized modules 75 in an upper left hand quadrant I, sixteen equal sized modules 76 in an upper right hand quadrant II, sixteen modules 74 in a lower left hand quadrant III, and sixteen modules 77 in a lower right hand quadrant IV. The shape and dimension of each module can, if desired, vary. However, in FIG. 9 each module 74, 75, 76, 77 has an equivalent shape and dimension. Adjacent modules 75 in the upper left hand quadrant are spaced equal distances apart, as are adjacent modules 75 to 77 in the remaining three quadrant illustrated in FIG. 9. If desired, module matrix 72 can, and likely would, include additional modules, preferably, but not necessarily, in sub-matrix groupings of four by four (or sixteen total) modules.

One particular advantage of module matrix 172 is that each quadrant I, II, III, IV of sixteen modules is spaced apart from any adjacent modules such that the distance indicated by arrows D5 and D7 is greater than the distance D6 between modules in a quadrant. This facilitates folding or cutting device 70 along axis X and/or Y.

Figure 11A:
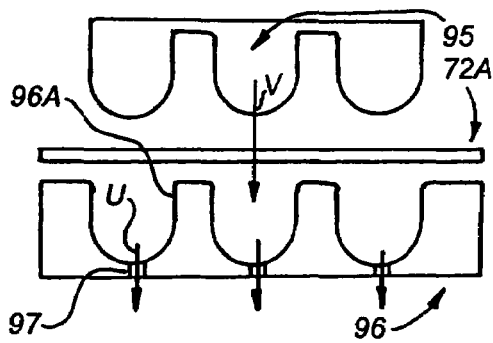
FIG. 11A is a front section view illustrating the first step in producing a module matrix used in the invention.
Figure 11B:
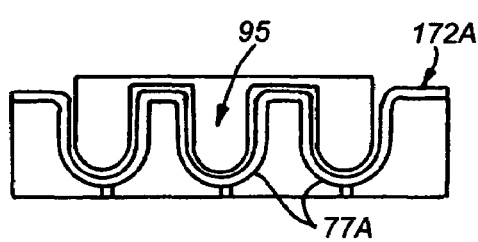
FIG. 11B is a front section view illustrating the second step in producing a module matrix used in the invention.
Figure 11C:
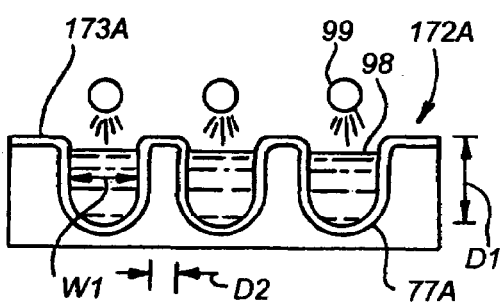
FIG. 11C is a front section view illustrating charging a module matrix with fluid.

Another advantage of module matrix 172 is that each module 74 to 77 has a semi-spherical, cylindrical, semi-ellipsoidal, semi-spheroidal or other arcuate bottom like modules 77A in FIGS. 11B and 11C. Providing modules 74 to 77 with arcuate bottoms faciliates pliably bending or deforming device 70 in the manner indicated by arrows 201 and 202 in FIG. 10D for heat transfer device 170. The arcuate bottoms of each module 74 to 77 also facilitate the flow of fluid around the bottoms.

The peripheral edges of seal layer 71 are fixedly sealingly connected to lips 88, 89 to seal liquid (not visible in FIG. 9) that fills pan 73 and surrounds modules 74, 75, 76, 77 and that fills each module 74, 75, 76, 77. Layer 71 is sealingly affixed to edges 88 and 89 in the same manner that layer 71A is affixed to edges 89A and 88A in FIG. 10D.

While distance D5 can vary as desired, D5 is presently preferably in the range of 16 mm to 24 mm. The distance D6, D2, D8 between a pair of adjacent modules 74 in a quadrant can vary but is presently preferably eight millimeters to twelve millimeters. The diameter or width W1 (FIG. 11C) of a module can vary but is presently preferably in the range of 20 mm to 40 mm. The depth D1 (FIG. 11C) of a module is preferably equal to or about equal to the width of the module. The bottom 77C (FIG. 10D) of a module can contact or need not contact the bottom 78, 78A of a pan 73, 173A.

A procedure for fabricating a heat transfer device similar to that depicted in FIG. 9 is illustrated FIGS. 10A to 10D and 11A to 11C.

Figure 10A:
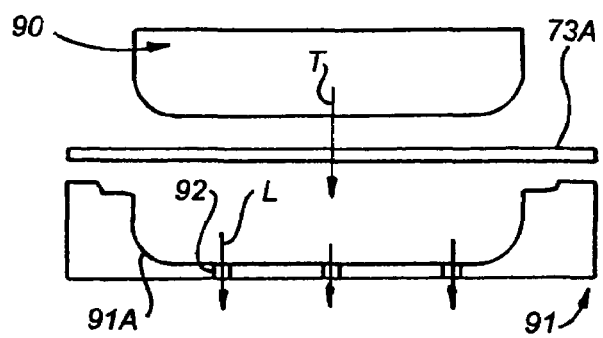
FIG. 10A is a front section view view illustrating the first step in a method for making a pan member used in the invention.

In FIG. 10A, a deformable pliable sheet 73A of a polymer or some other material is provided along with a mold 91. Mold 91 includes apertures 92. Apparatus (not shown) draws air out from the inside of mold 91 through apertures 92 in the direction indicated by arrow L to draw sheet 73A into the mold and to contour sheet 73A to the inner surface 91A of the mold. A follower 90 is also provided to assist sheet 73A in contouring to surface 91A. After suction is applied to draw air in the direction of arrow L and follower 90 is simultaneously moved downwardly in the direction of arrow T, sheet 73A contours to inner surface 91A in the manner illustrated in 10B and a pan 173A is formed.

Figure 10B:
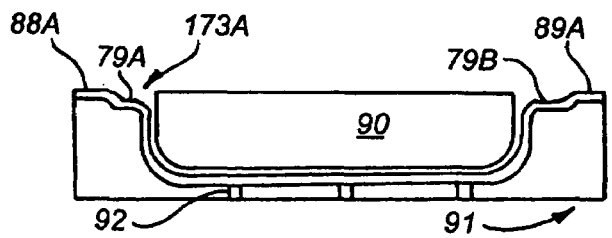
FIG. 10B is a front section view illustrating the second step in a method for making a pan member used in the invention.

In FIG. 10B, pan 173A includes bottom 78A, includes elongate, parallel spaced apart inset edges 79A and 79B, and includes elongate, parallel, spaced apart outer edges 88A and 89A.

Figure 10C:
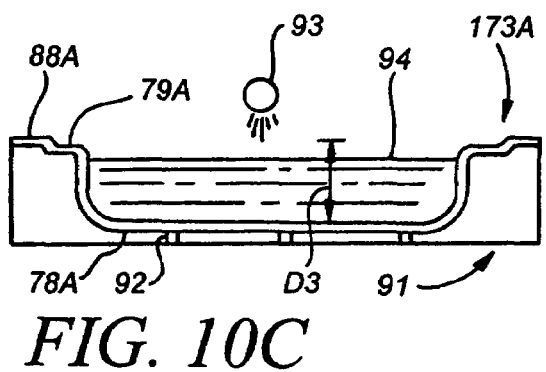
FIG. 10C is a front section view illustrating the administration of fluid to the pan member of FIG. 10B.

In FIG. 10C, follower 90 has been removed and nozzle 93 is utilized to inject fluid into pan 173A to form a reservoir 94.

Figure 10D:
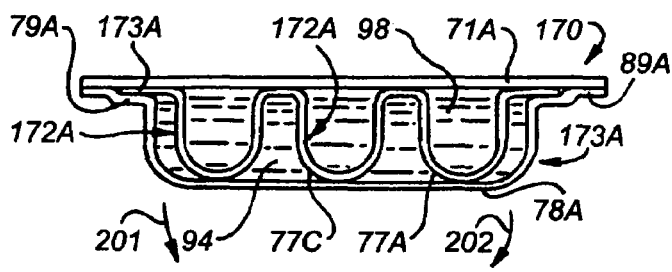
FIG. 10D is a front section view illustrating the incorporation and sealing of a module matrix into the pan member—fluid system of FIG. 10C.

The module matrix 172A produced using the steps illustrated in FIGS. 11A to 11C is inserted in pan 173A in FIG. 10D.

In FIG. 11A, a deformable pliable sheet 72A of a polymer or some other material is provided along with a mold 96. Mold 96 includes openings 97. Each opening 97 includes an upright cylindrical wall and a semi-spherical bottom. Apparatus (not shown) draws air out from the inside of mold 96 through apertures 97 in the direction indicated by arrow U to draw sheet 72A into the mold and to contour sheet 72A to the inner surfaces 96A of the mold. A follower 95 is also provided to assist sheet 72A in contouring to cupped surfaces 96A. After suction is applied to draw air in the direction of arrow U and follower 95 is simultaneously moved downwardly in the direction of arrow V, sheet 72A is contoured to inner surfaces 96A in the manner illustrated in 11B and a module matrix 172A is formed.

In FIG. 11B, module matrix 172A includes modules 77A.

In FIG. 11C, follower 95 has been removed and nozzles 99 are utilized to inject fluid into modules 77A to form a reservoir 98 in each module 77A. The fluid charged module matrix 172A is inserted in the pan 173A of FIG. 10 to produce the module matrix 172A—pan 173A combination illustrated in FIG. 10D. After the module matrix 172A is inserted in pan 173A in the manner illustrated in FIG. 10D, a layer 71A is applied to seal the fluid reservoirs 98, 94 to complete the production of a heat transfer device in accordance with the invention. Layer 71A is continuously sealed to outer edges 88A and 89A.

If desired, module matrix 172A can be inserted in the pan 173A of FIG. 10C before each module 77A is charged with fluid to form reservoirs 98. Or, a auxiliary layer similar to layer 71A can be applied to module matrix 172A before matrix 172A is inserted in pan 173A. This auxiliary layer would seal fluid reservoirs 98 in the matrix 172A. After this sealed matrix 172A is inserted in pan 173A, then layer 71A is applied to seal matrix 172A and reservoir 94 in pan 173A.

As earlier discussed, the fluid in reservoirs 98 normally preferably has a different freezing tempering than the fluid in reservoir 94.

In FIG. 9, the fluid in pan 73 and the fluid in each module 74 to 77 has been omitted for the sake of clarity. The structure of the heat transfer device 70 of FIG. 9 is generally equivalent to the structure of the heat transfer device illustrated in FIG. 10D except, of course, that the heat transfer device in FIG. 10D includes fewer modules than the heat transfer device 70.

Figure 12:
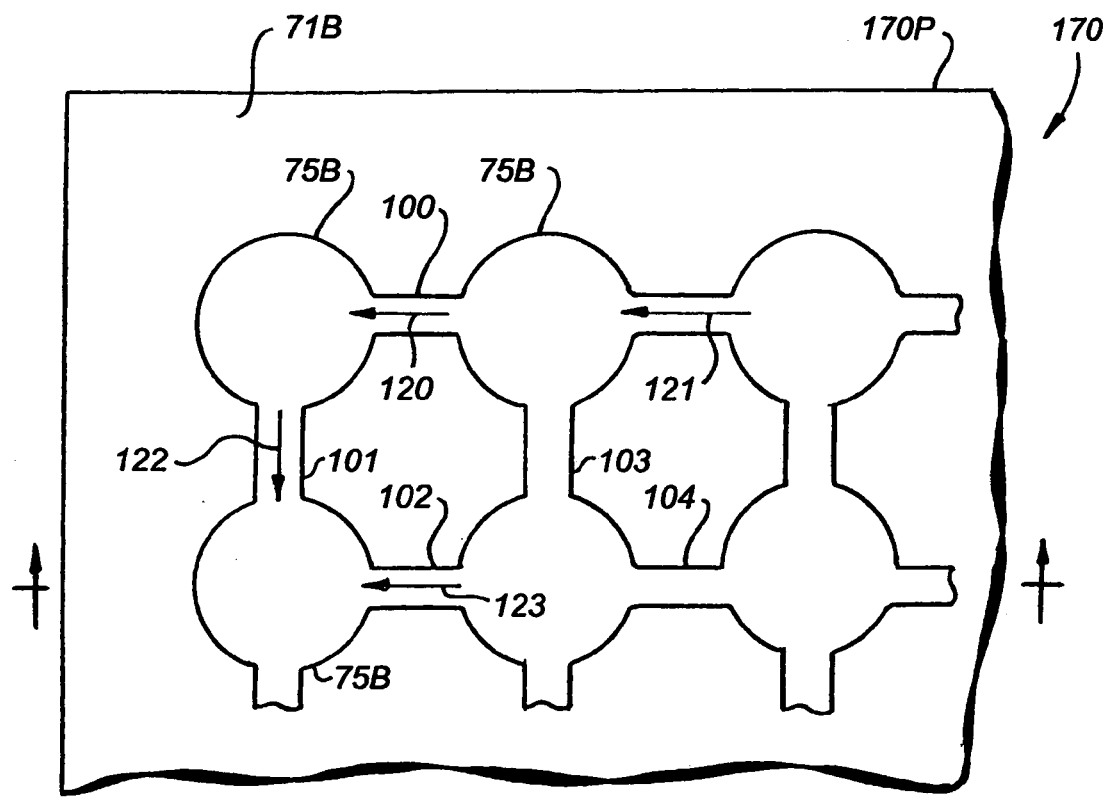
FIG. 12 is a top view illustrating still another embodiment of the invention; and, FIG. 13 is a side section view of the apparatus of FIG. 12 and illustrating additional construction features thereof.
Figure 13:
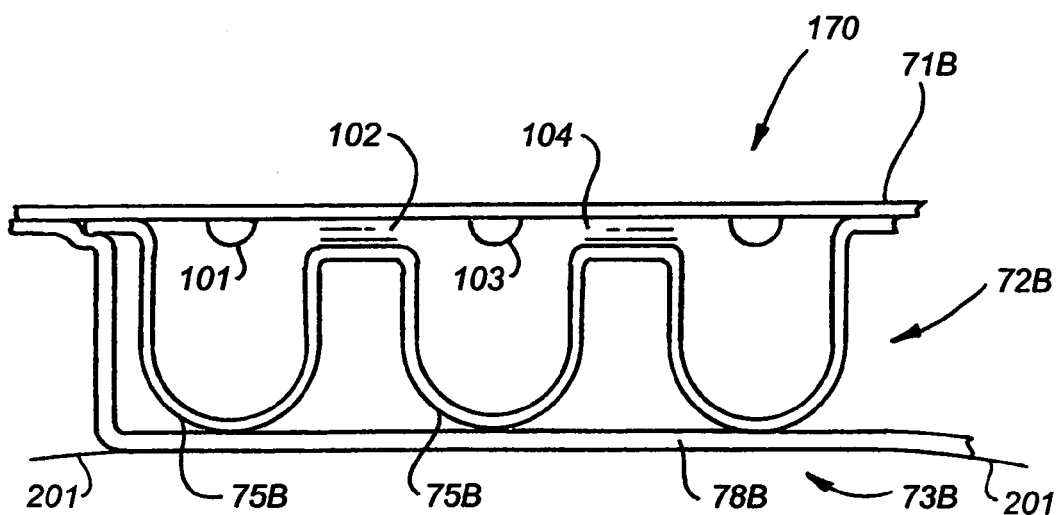

FIGS. 12 and 13 illustrate another heat transfer device 170 constructed in accordance with the invention. Device 170 is generally equivalent in structure to heat transfer device 70 and to the heat transfer device of FIG. 10D except that modules 75B in the module matrix 72B are interconnected by semi-cylindrical channels 100, 102, 104. Device 170 includes sealing layer 71B and pan 73B with bottom 78B. The bottom of each module 75B contacts bottom 78B as illustrated in FIG. 13. It is not, however, necessary that the bottom of each module 75B contact bottom 78B. Each module 75B is charged with a liquid (not shown), and pan 73B is charged with a liquid (not shown). The liquid in modules 75B has a different freezing temperature than the liquid in pan 73B. When device 170 is utilized, the liquid in modules 75B near the peripheral edge 170P of device 170 tends to melt first. Since channels 100, 102, 104 permit fluid to flow between modules 75B, channels 100, 102, 104 are believed to facilitate a more uniform distribution of heat into or from device 170. As would be appreciated by those of skill in the art, in FIG. 11A, mold 96 can be shaped and dimensioned to produce a module matrix 172A that would include channels 100, 102, 104. Bottom 78B contacts and conforms to the contour of the exterior portion 201 of an individual's body.

Having described my invention in such terms as to enable those of skill in the art to make and practice it, and having described the presently preferred embodiments thereof,

I claim:

1. In combination with a heat generating exterior portion of the body of an individual, said exterior portion having an arcuate contour, improvements for removing heat from said exterior portion, said improvements comprising a cooled heat transfer device to draw heat away from and cool the exterior portion of the body, the improvements including
   (a) a pliable water impermeable outer wall
      (i) circumscribing and enclosing an inner space, and
      (ii) positioned above the exterior portion of the body of the individual, said wall including
      (iii) a pan (73B) with a bottom (78B) contacting and conforming to the contour of the exterior portion of the body of the individual, and
      (iv) a sealing layer (71B);
   (b) a plurality of spaced apart hollow fluid tight modules (75B) extending from said sealing layer into said inner space and toward said bottom (78B), each of said hollow modules including
      (i) a pliable thin-walled bottom portion,
      (ii) a thin-walled side interconnecting said bottom portion and sealing layer,
      (iii) an inner space, and
      (iv) an outer surface area;
   (c) a first heat-exchange composition in said inner space contacting said outer surface area of each of said fluid tight modules and comprising a first liquid which undergoes a change of state from the liquid phase to the solid phase at a selected temperature of transformation less than fifteen degrees F., said selected temperature of transformation being lower than the coldest temperatures found in conventional household freezers;
   (d) a second heat-exchange composition in said inner space of each of said modules and comprising a frozen second liquid which undergoes a change of state from a liquid phase to a frozen solid phase at a temperature in the range of fifteen degrees to thirty-two degrees F., said second fluid having a freezing point that is higher than the freezing point of said first fluid, said heat transfer device having (i) a surface temperature at least as cool as ten degrees F., and, when placed on a table at an ambient temperature of eighty degrees, which warms after four hours to a temperature no warmer than forty-two degrees F.,
(ii) an interior temperature
at least as cool as fifteen degrees F., and,
when placed on a table at an ambient temperature of eighty degrees,
which warms after four hours to a temperature no warmer than thirty-six degrees;
(e) convection currents in said first fluid moving upwardly away from the exterior portion of the individual's body as the result of heat absorbed by said first liquid; and,
(f) a plurality of channels each
(i) interconnecting a pair of said pliable hollow modules to permit the flow of liquid therebetween,
(ii) extending from said side of each of said pair of said hollow modules, and
(iii) extending along said sealing layer.

2. The combination of claim 1 wherein said bottom portion of each of said containers is rounded.

3. The combination of claim 1 wherein said bottom portion of each of said containers contacts said bottom of said pan.

* * * * *